US00PP07822P

United States Patent [19]

Scott

[11] Patent Number: Plant 7,822

[45] Date of Patent: Mar. 10, 1992

[54] *PLUMBAGO AURICULATA* CV. MONOTT

[75] Inventor: Paul L. Scott, Duarte, Calif.

[73] Assignee: Monrovia Nursery Company, Azusa, Calif.

[21] Appl. No.: 591,365

[22] Filed: Oct. 1, 1990

[51] Int. Cl.[5] ..... A01H 5/00

[52] U.S. Cl. ..... Plt./54

[58] Field of Search ..... Plt./54

*Primary Examiner*—James R. Feyrer

[57] ABSTRACT

A new and distinct selection of Plumbago shrub which shall be referred to hereinafter as *Plumbago auriculata* cultivar Monott. *Plumbago auriculata* cultivar Monott differs distinctively from other *Plumbago auriculata* plants by its unique combination of its floriferous habit of rich blue flowers and larger and wider petals and a more dense compact growth habit.

1 Drawing Sheet

BACKGROUND OF THE NEW PLANT

This invention relates to a new and distinct selection of *Plumbago auriculata,* a member of the Plumbaginaceae or Leadwort Family. *Plumbago auriculata* cultivar Monott was discovered in a group of my seedlings in the summer of 1988 on my property in Duarte. These seedlings were openly pollenated.

My new plant has been asexually reproduced by cuttings by me on my Duarte property and by Monrovia Nursery Company. The distinct phenotypic characteristics of my new selection that sets this plant apart from other *Plumbago auriculata* plants could be lost genetically through sexual reproduction. Therefore, sexual reproduction is prohibited and propagation is restricted to asexual reproduction by cuttings.

SUMMARY OF INVENTION

*Plumbago auriculata* cv. Monott is different and outstanding. The average and typical seedling *Plumbago auriculata* which is readily available for landscaping has a pale blue flower ranging in colors of Pastel Lilac 437/3 to Bluebird Blue 042/2. My selection has a rich blue color of the flowers which are noticeably larger and which sets my plant apart from other *Plumbago auriculata* plants.

My new selection is extremely floriferous for eight months of the year in Southern California. The growth habit though up to 5 feet in height and width does have a more dense habit and is slightly smaller than the typical sprawling Plumbago seedlings.

'Monott' is characterized and distinguished by being more precocious and concentrated in flowering habit, and as having a more compact growth habit when compared with other members of the species. These characteristics are noticable in, for example, responses to pruning, where specimens of the claimed plant and comparison plants of the species were pruned in early August. By early October, the plants of the species had flushed in growth and produced only scant flower buds and flowers, with specimens being predominantly green in coloration. Meanwhile, specimens of 'Monott' had also flushed growth, but to a much lesser degree, and were covered with heavy bud and bloom, rendering an appearance of a distinct blue coloration when viewed from a distance. In close observation, it was noted that the internodes of the plants of the comparison were substantially equal in length, but representative plants of the species had produced about 18–22 cm of terminal growth from the points of pruning, while 'Monott' had produced only about 10–15 cm of terminal growth from the points of pruning. This comparison illustrates the propensity of 'Monott' to conspicuously grow less and flower more, and its greater ability to direct its energy into the production of flowers, earlier, rather than vegetative growth when compared to the species when grown under the same conditions.

BRIEF DESCRIPTION OF DRAWINGS

The above photo exhibits the characteristic deeper blue flowers.

The photo below depicts the overall habit and flower color differences of a seedling versus my new selection. My selection on the left exhibits the rich blue flowers and larger and wider petals.

BOTANICAL DESCRIPTION

Below is a detailed description of my new selection of *Plumbago auriculata* cv. Monott, the color terminology is from the British Horticultural Color Charts.

Overall size and habit: Mounding shrub. After 5 years plant should achieve a height of about 5 feet and a spread of 5 feet.

This plant grows at a slower rate than comparison plants of the species due to its higher level of bud and flower production. Internode lengths of 'Monott' are substantially equal to those of the species, but less terminal growth is made with flower numbers being about four times that of plants typical of the species. The heavier flowering of this selection results in a plant which is comparatively more compact through its growth, and, while flowering peaks early in the season, 'Monott' continuously presents a higher level of bloom resulting in a more attractive, colorful appointment where it is used for landscape purposes, as compared to other members of the species.

Tolerance to drought: When established in the landscape *Plumbago auriculata* is very tolerant of dry situations.

Flower: In Southern California flowers appear from April through November.

The flower parts of the plant of this disclosure, 'Monott' are substantially identical to those of the species per se, but are presented in numbers which are in the order of four times as numerous as those of typical specimens of the species when observed at any point of the growing season.

Arrangement.—In terminal, spikelike racemes.

*Color.*—Petals — Gentian Blue 42/1. Petal midrib — Hyacinth Blue 40. Note: Color may vary slightly due to weather conditions, lighter in hot dry, deeper in cool moist climates.

*Size.*—Length: 2.5–3.0 cm. Diameter: 2.5–2.8 cm.

*Shape.*—Corolla tube slender, lobes 5, spreading.

Leaf:

*Arrangement:* The coloration of new and mature foliage of 'Monott' is substantially identical to that of comparison plants of the species. When observed from a distance, the foliage of 'Monott' is distinctly less conspicuous in all seasons due to being masked to a higher degree by its greater number of flowers. Alternate.

*Size.*—Length 5.8 cm to 4.0 cm, width 2.2 cm to 1.4 cm, leaves arising from leaf axils are smaller.

Color.—Upper — Spinach Green 0960/1. Lower — Spinach green 0960/2.

*Shape.*—Spatulate.

*Margins.*—Entire, undulate.

Fruit: 5 parted capsule. Seeds produced by the plant of this disclosure are substantially identical to those produced by typical specimens of the species in terms of size and appearance, and are fertile.

I claim:

1. A new and distinct variety of Plumbago plant as substantially shown and described herein, that is characterized particularly as a novelty by the unique combination of its floriferous habit of rich blue flowers and larger and wider petals and a more dense compact growth habit.

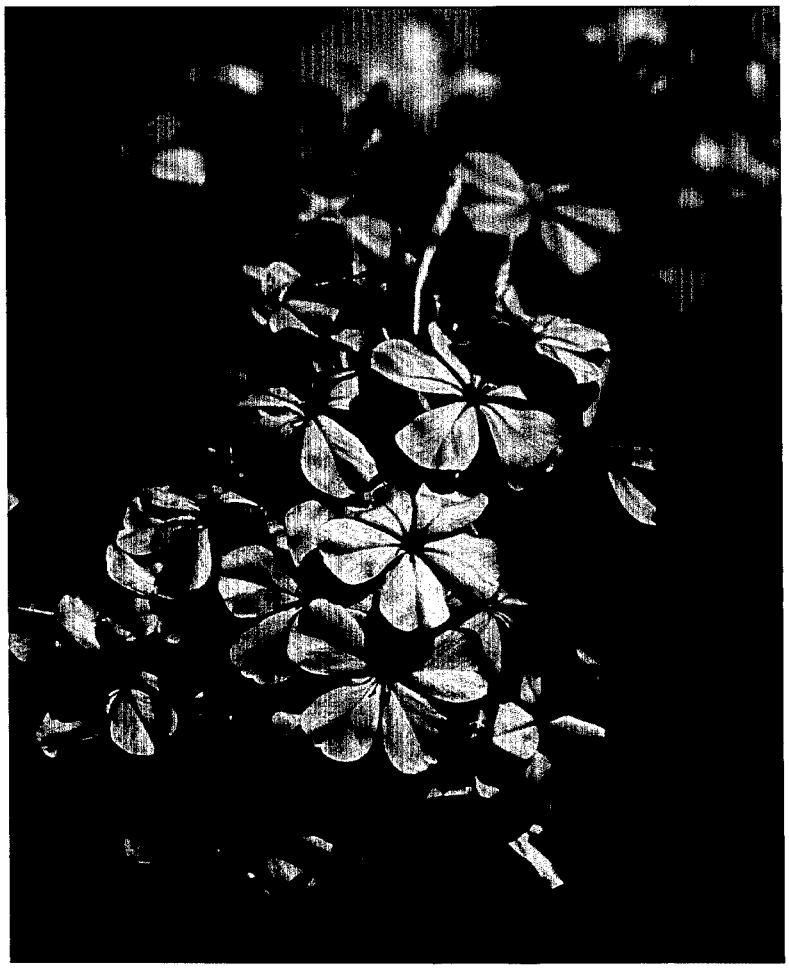
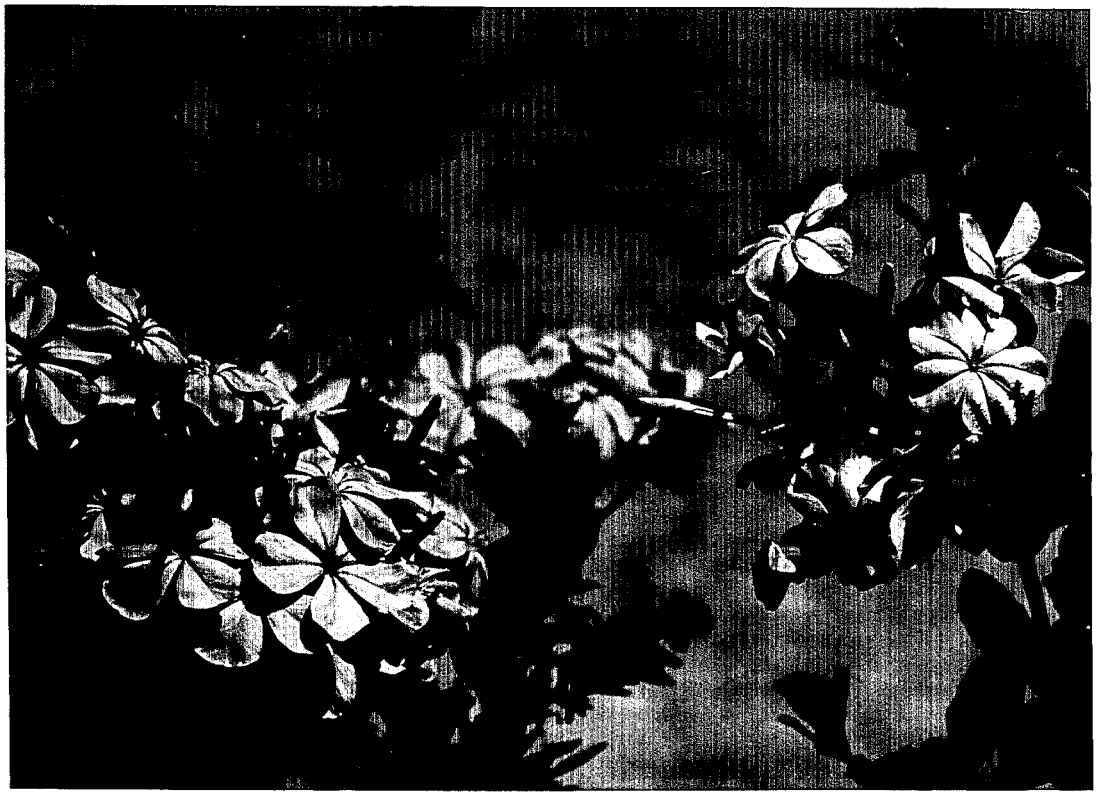

* * * * *